United States Patent
Chang et al.

(10) Patent No.: US 6,224,748 B1
(45) Date of Patent: *May 1, 2001

(54) PROCESS FOR HYDROCRACKING CYCLE OIL

(75) Inventors: Clarence D. Chang, Princeton; Scott Han, Lawrenceville, both of NJ (US); Daniel J. Martenak, Dublin, PA (US); Jose G. Santiesteban, Yardley, PA (US); Dennis E. Walsh, Richboro, PA (US)

(73) Assignee: Mobil Oil Corporation, Fairfax, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/169,107

(22) Filed: Dec. 20, 1993

Related U.S. Application Data

(63) Continuation-in-part of application No. 08/150,304, filed on Nov. 12, 1993, which is a continuation-in-part of application No. 08/095,884, filed on Jul. 22, 1993, now abandoned, and a continuation-in-part of application No. 08/150,303, filed on Nov. 12, 1993.

(51) Int. Cl.$^7$ ............................. C10G 47/02; C10G 47/04
(52) U.S. Cl. ..................... 208/112; 208/106; 208/107; 208/108; 208/113; 208/121
(58) Field of Search .................... 208/106, 107, 208/108, 112, 113, 121

(56) References Cited

U.S. PATENT DOCUMENTS

| | | | |
|---|---|---|---|
| 3,755,147 | * 8/1973 | Michelson | 208/112 |
| 3,803,028 | * 4/1974 | Mead et al. | 208/111 |
| 3,956,105 | * 5/1976 | Conway | 208/112 |
| 4,283,272 | 8/1981 | Garwood et al. | 208/59 |
| 4,676,887 | 6/1987 | Fischer et al. | 208/61 |
| 4,738,766 | 4/1988 | Fischer et al. | 208/68 |
| 4,783,575 | 11/1988 | Schmidt et al. | 585/748 |
| 4,789,457 | 12/1988 | Fischer et al. | 208/68 |
| 4,918,041 | 4/1990 | Hollstein et al. | 502/217 |
| 4,921,594 | * 5/1990 | Miller | 208/111 |
| 5,113,034 | 5/1992 | Soled et al. | 585/510 |

FOREIGN PATENT DOCUMENTS 1288339   11/1989 (JP).

OTHER PUBLICATIONS

*Proceedings 9th International Congress on Catalysis*, vol. 4, 1727–1735 (1988), K. Arata and M. Hino.

Hino and Arata, "Synthesis of Solid Superacid of Tungsten Oxide Supported on Zirconia and Its Catalytic Action for Reactions of Butane and Pentane", J. Chem. Soc., Chem. Commun., 1259–1260 (1988).

* cited by examiner

*Primary Examiner*—Elizabeth Wood
(74) *Attorney, Agent, or Firm*—Malcolm D. Keen

(57) ABSTRACT

A process for hydrocracking heavy, high aromatic content feeds, such as cycle oil, using a catalyst composition containing a hydrogenation/dehydrogenation component, such as a noble metal, and an acidic solid component including a Group IVB metal oxide modified with an oxyanion of a Group VIB metal.

16 Claims, No Drawings

PROCESS FOR HYDROCRACKING CYCLE OIL

CROSS-REFERENCE TO RELATED APPLICATIONS

This application is a continuation-in-part of co-pending application Ser. No. 08/150,304, filed Nov. 12, 1993, entitled "A Process For Selective Wax Hydrocracking," which is a continuation in part of Ser. No. 08/095,884 filed Jul. 22, 1993 now abandoned, entitled "Paraffin Isomerization Catalyst and Process for Its Use" incorporated herein in its entirety by reference. This application is further related by subject matter to co-pending application Ser. No. 08/150,303, filed Nov. 12, 1993, entitled "A Process for Naphtha Hydrocracking".

FIELD OF THE INVENTION

The process of the present invention relates to a process for hydrocracking cycle oils and other highly aromatic feeds using a catalyst comprising a hydrogenation/dehydrogenation component, such as a noble metal, and an acidic solid component comprising a Group IVB metal oxide modified with an oxyanion of a Group VIB metal.

BACKGROUND OF THE INVENTION

U.S. Pat. No. 4,676,887 discloses refining of petroleum hydrocarbons to product motor fuels and other products. The process described in U.S. Pat. No. 4,676,887 operates by hydrocracking a highly aromatic feed which is produced by catalytic cracking of a suitable petroleum fraction, usually a vacuum gas oil. During the catalytic cracking the dealkylation processes characteristic of the catalytic cracking process remove alkyl groups from the polyaromatic materials in the feed to produce the gasoline as the main product together with various other higher boiling fractions. A highly aromatic distillate fraction formed in the cracking and boiling from about 400° F. to 750° F. (about 205° to 400° C.), generally referred to as cycle oil, forms a preferred feed for the subsequent hydrocracking step which converts the bicyclic aromatics (naphthalenes) in the oil under relatively mild conditions to monocyclic aromatics in the gasoline boiling range. In this way, the cycle oil from the cracking process is converted to a gasoline range product, which, being highly aromatic, has a high octane value and can therefore be incorporated directly into the refinery gasoline pool without the need for subsequent reforming. The process uses relatively mild conditions e.g., hydrogen pressure under 1000 psig, (about 7000 kPa abs) and moderate conversion coupled with an acceptably low catalyst aging rate so that long cycle durations may be obtained. Reference is made to U.S. Pat. No. 4,676,887 for a detailed description of the process.

As mentioned above, a cycle oil from the catalytic cracking step is used as the feed to the hydrocracking step and usually a light cycle oil boiling approximately in the range of 400° to 700° F. (about 205° to 400° C.) is suitable. However, if a light cut-light cycle oil with an end point of not more than about 650° F. (345° C.), preferably not more than about 600° C. (about 315° C.) is used, it is possible to operate at higher conversion levels without a concomitant increase in hydrogen pressure while still maintaining an acceptable aging rate in the catalyst. In addition, the octane rating of the hydrocracked gasoline is higher. Thus, by suitable choice of the hydrocracker feed, an extended range of operating conditions may be utilized while improving product quality. The use of the light cut light, cycle oil in this process is disclosed in U.S. Pat. No. 4,738,766, to which reference is made for a detailed disclosure of the process.

Because the hydrocracking is operated under relatively low hydrogen pressure, conversion is maintained at a relatively moderate level in order to maintain catalyst aging at an acceptable rate. One consequence of this is that the effluent from the hydrocracker contains significant quantities of unconverted material, i.e. products boiling above the gasoline boiling range. The hydrocracking step has effected a removal of a significant amount of the heteroatom containing impurities in the cycle oil feed and this is reflected by relatively low sulfur and nitrogen contents in the gasoline conversion product as well as in the higher boiling fractions. In addition, some of the higher boiling fractions have undergone hydrogenation to form more readily crackable components, and for this reason a useful aspect of the process is in the recycle of the unconverted hydrocracker bottoms to the catalytic cracking unit. A process of this type is disclosed in U.S. Pat. No. 4,789,457 to which reference is made for a detailed description of the process.

We have now found that solid acid catalysts comprising a Group IVB metal oxide modified with an oxyanion of a Group VIB metal may be used as hydrocracking catalysts for cycle oil and other highly aromatic feeds. It is an object of the present invention to provide a hydrocracking process using a catalyst which results in significant boiling range conversion of heavier cycle oil components to lighter liquids and with low production of $C_1$–$C_4$ gases.

SUMMARY OF THE INVENTION

There is described herein a catalytic process for hydrocracking heavy, high aromatic content feeds, such as cycle oil. Processing a light cycle oil feed over a catalyst comprising a Group IVB metal oxide modified with an oxyanion of a Group VIB metal results in significant boiling range conversion, particularity of heavier cycle oil components (600° F.+) to lighter liquids. Under the hydrocracking process of the present invention only small amounts of light gases are formed. Hydrogen enrichment and preservation of the upgraded liquid products have also been found using the catalyst of the present invention.

The invention therefore includes a process for hydrocracking a hydrocarbon feedstock having an initial boiling point above about 400° F. and an aromatic content greater than about 50 wt. % comprising hydrocracking the hydrocarbon feedstock in the presence of hydrogen at a pressure of at least about 1000 psig in the presence of a catalyst composition comprising
a hydrogenation/dehydrogenation component and an acidic solid component comprising a Group IVB metal oxide modified with an oxyanion of a Group VIB metal.

DETAILED DESCRIPTION OF THE INVENTION

Feedstocks

The feed to the process is a highly aromatic stream such as a light cycle oil produced by catalytic cracking, usually by the fluid catalytic cracking (FCC) process. The feedstock will have a hydrogen content no greater than 12.5 wt. % and an API gravity no greater than about 25, usually no greater than about 20 and an aromatic content no less than about 50 wt. %. Typically the feed will have an API gravity of 5 to 25, a nitrogen content of 50 to 650 ppm and will contain 8.5 to 12.5 wt. % hydrogen. The boiling range of the feedstock will usually be from about 400 to 800° F. (205 to 370° C.), more commonly 400 to 700° F. (205 to 370° C.). Suitable feeds include, but are not limited to, light cycle oil (LCO) and heavy cycle oil (HCO) from catalytic crackers, lube extracts, and coker gas oils.

The hydrocarbon feedstock can be treated prior to hydrocracking in order to reduce or substantially eliminate its heteroatom content. As necessary or desired, the feedstock can be hydrotreated under mild or moderate hydroprocessing conditions to reduce its sulfur, nitrogen, oxygen and metal content. Generally, a hydrocarbon feedstock used in hydrocracking should have a low metals content, e.g., less than about 200 ppm, in order to avoid obstruction of the catalyst and plugging of the catalyst bed. The mild to moderate hydrotreating conditions employed include pressures of from about 2 to about 21 MPa and $H_2$ consumptions of from about 20 to about 280 $m^3/m^3$. Conventional hydrotreating process conditions and catalysts can be employed, e.g., those described in U.S. Pat. No. 4,283,272, the contents of which are incorporated by reference herein.

Catalyst

The catalyst used in the process of the present invention comprises an oxide of a Group IVB metal, preferably zirconia or titania. This Group IVB metal oxide is modified in two ways. According to one modification, the Group IVB metal oxide is modified with an oxyanion of a Group VIB metal, such as an oxyanion of tungsten, such as tungstate. The modification of the Group IVB metal oxide with the oxyanion of the Group VIB metal imparts acid functionality to the material. The modification of a Group IVB metal oxide, particularly, zirconia, with a Group VIB metal oxyanion, particularly tungstate, is described in U.S. Pat. No. 5,113,034; in Japanese Kokai Patent Application No. Hei 1 [1989]-288339; and in an article by K. Arata and M. Hino in *Proceedings 9th International Congress on Catalysis,* 4, 1727–1735 (1988), the entire disclosures of these publications are expressly incorporated herein by reference.

According to another modification of the Group IVB metal oxide described herein, a hydrogenation/dehydrogenation component is combined with the Group IV metal oxide. This hydrogenation/dehydrogenation component imparts the ability of the material to catalyze the addition of hydrogen to or the removal of hydrogen from organic compounds, such as hydrocarbons, optionally substituted with one or more heteroatoms, such as oxygen, nitrogen, metals or sulfur, when the organic compounds are contacted with the modified material under sufficient hydrogenation or dehydrogenation conditions.

Examples of hydrogenation/dehydrogenation components include the oxide, hydroxide or free metal (i.e., zero valent) forms of Group VIII metals (i.e., Pt, Pd, Ir, Rh, Os, Ru, Ni, Co and Fe), Group IVA metals (i.e., Sn and Pb), Group VB metals (i.e., Sb and Bi) and Group VIIB metals (i.e., Mn, Tc and Re). The catalyst may comprise one or more catalytic forms of one or more noble metals (i.e., Pt, Pd, Ir, Rh, Os or Ru). Combinations of catalytic forms of such noble or non-noble metals, such as combinations of Pt with Sn, may be used. The valence state of the metal of the hydrogenation/dehydrogenation component is preferably in a reduced valance state, e.g., when this component is in the form of an oxide or hydroxide. The reduced valence state of this metal may be attained, in situ, during the course of a reaction, when a reducing agent, such as hydrogen, is included in the feed to the reaction.

For the purposes of the present disclosure, the expression, Group IVB metal oxide modified with an oxyanion of a Group VIB metal, is intended to connote a material comprising, by elemental analysis, a Group IVB metal, a Group VIB metal and oxygen, with more acidity than a simple mixture of separately formed Group IVB metal oxide mixed with a separately formed Group VIB metal oxide or oxyanion. The present Group IVB metal, e.g., zirconium, oxide modified with an oxyanion of a Group VIB metal, e.g., tungsten, is believed to result from an actual chemical interaction between a source of a Group IVB metal oxide and a source of a Group VIB metal oxide or oxyanion.

This chemical interaction is discussed in the aforementioned article by K. Arata and M. Hino in *Proceedings 9th International Congress on Catalysis,* 4, 1727–1735 (1988). In this article, it is suggested that solid superacids are formed when sulfates are reacted with hydroxides or oxides of certain metals, e.g., Zr. These superacids are said to have the structure of a bidentate sulfate ion coordinated to the metal, e.g., Zr. In this article, it is further suggested that a superacid can also be formed when tungstates are reacted with hydroxides or oxides of Zr. The resulting tungstate modified zirconia materials are theorized to have an analogous structure to the aforementioned superacids comprising sulfate and zirconium, wherein tungsten atoms replace sulfur atoms in the bidentate structure.

Although it is believed that the present catalysts may comprise the bidentate structure suggested in the aforementioned article by Arata and Hino, the particular structure of the catalytically active site in the present Group IVB metal oxide modified with an oxyanion of a Group VIB metal has not yet been confirmed, and it is not intended that this catalyst component should be limited to any particular structure.

Other elements, such as alkali (Group IA) or alkaline earth (Group IIA) compounds may optionally be added to the present catalyst to alter catalytic properties. The addition of such alkali or alkaline earth compounds to the present catalyst may enhance the catalytic properties of components thereof, e.g., Pt or W, in terms of their ability to function as a hydrogenation/dehydrogenation component or an acid component.

The Group IVB metal (i.e., Ti, Zr or Hf) and the Group VIB metal (i.e., Cr, Mo or W) species of the present catalyst are not limited to any particular valence state for these species. These species may be present in this catalyst in any possible positive oxidation value for these species. Subjecting the catalyst, e.g., when the catalyst comprises tungsten, to reducing conditions, e.g., believed to be sufficient to reduce the valence state of the tungsten, may enhance the overall catalytic ability of the catalyst to catalyze certain reactions, e.g., the hydrocracking of waxy feeds.

Suitable sources of the Group IVB metal oxide, used for preparing the present catalyst, include compounds capable of generating such oxides, such as oxychlorides, chlorides, nitrates, etc., particularly of zirconium or titanium. Alkoxides of such metals may also be used as precursors or sources of the Group IVB metal oxide. Examples of such alkoxides include zirconium n-propoxide and titanium i-propoxide. Preferred sources of a Group IVB metal oxide are zirconium hydroxide, i.e., $Zr(OH)_4$, and hydrated zirconia. The expression, hydrated zirconia, is intended to connote materials comprising zirconium atoms covalently linked to other zirconium atoms via bridging oxygen atoms, i.e., Zr—O—Zr, further comprising available surface hydroxy groups. These available surface hydroxyl groups are believed to react with the source of an anion of a Group IVB metal, such as tungsten, to form the present acidic catalyst component. As suggested in the aformentioned article by K. Arata and M. Hino in *Proceedings 9th International Congress on Catalysis,* 4, 1727–1735 (1988), precalcination of $Zr(OH)_4$ at a temperature of from about 100° C. to about 400° C. results in a species which interacts more favorably with tungstate. This precalcination is believed to result in the condensation of ZrOH groups to form a polymeric zirconia species with surface hydroxyl groups. This polymeric species is referred to herein as a form of a hydrated zirconia.

Treatment of hydrated zirconia with a base solution prior to contact with a source of tungstate may be preferable. More particularly, as demonstrated in Examples recited hereinafter, especially in Examples 16–25, refluxing hydrated zirconia in an $NH_4OH$ solution having a pH of greater than 7 was beneficial. Without wishing to be bound by any theory, it is theorized that the base-treated, hydrated zirconia is better because it has higher surface area. It is also theoretically possible that the base treatment alters surface hydroxyl groups on the hydrated zirconia, possibly in a manner which promotes a more desirable interaction with the source of tungstate later used.

Suitable sources for the oxyanion of the Group VIB metal, preferably molybdenum or tungsten, include, but are not limited to, ammonium metatungstate or metamolybdate, tungsten or molybdenum chloride, tungsten or molybdenum carbonyl, tungstic or molybdic acid and sodium tungstate or molybdate.

The hydrogenation/dehydrogenation component of the present catalyst may be derived from Group VIII metals, such as platinum, iridium, osmium, palladium, rhodium, ruthenium, nickel, cobalt, iron and mixtures of two or more thereof. These components may optionally be mixed with components derived from Group IVA metals, preferably Sn, and/or components derived from Group VIIB metals, preferably rhenium and manganese. These components may be added to the catalyst by methods known in the art, such as ion exchange, impregnation or physical admixture. For example, salt solutions of these metals may be contacted with the remaining catalyst components under conditions sufficient to combine the respective components. The metal containing salt is preferably water soluble. Examples of such salts include chloroplatinic acid, tetraammineplatinum complexes, platinum chloride, tin sulfate and tin chloride.

The present catalyst may be prepared, for example, by impregnating the hydroxide or oxide, particularly the hydrated oxide, of the Group IVB metal with an aqueous solution containing an anion of the Group VIB metal, preferably tungstate or molybdate, followed by drying. Calcination of the resulting material may be carried out, preferably in an oxidizing atmosphere, at temperatures from about 500° C. to about 900° C., preferably from about 700° C. to about 850° C., and more preferably from about 750° C. to about 825° C. The calcination time may be up to 48 hours, preferably for about 0.5–24 hours, and more preferably for about 1.0–10 hours. In a most preferred embodiment, calcination is carried out at about 800° C. for about 1 to about 3 hours. The hydrogenation/dehydrogenation component of the catalyst (e.g., Group VIII metal, Group VIIB metal, etc.) may be added after or before the calcination step by techniques known in the art, such as impregnation, coimpregnation, coprecipitation, physical admixture, etc. The hydrogenation/dehydrogenation component may also be combined with the remaining catalyst components before or after these remaining components are combined with a binder or matrix material as described hereinafter.

When a source of the hydroxide or hydrated oxide of zirconium is used, calcination, e.g., at temperatures greater than 500° C., of the combination of this material with a source of an oxyanion of tungsten may be needed to induce the theorized chemical reaction which imparts the desired degree of acidity to the overall material. However, when more reactive sources of zirconia are used, it is possible that such high calcination temperatures may not be needed.

In the present catalyst, of the Group IVB oxides, zirconium oxide is preferred; of the Group VIB anions, tungstate is preferred; and of the hydrogenation/dehydrogenation components, platinum and/or platinum-tin are preferred.

Qualitatively speaking, elemental analysis of the present catalyst will reveal the presence of Group IVB metal, Group VIB metal and oxygen. The amount of oxygen measured in such an analysis will depend on a number of factors, such as the valence state of the Group IVB and Group VIB metals, the form of the hydrogenation/dehydrogenation component, moisture content, etc. Accordingly, in characterizing the composition of the present catalyst, it is best not to be restricted by any particular quantities of oxygen. In functional terms, the amount of Group VIB oxyanion in the present catalyst may be expressed as that amount which increases the acidity of the Group IVB oxide. This amount is referred to herein as an acidity increasing amount. Elemental analysis of the present catalyst may be used to determine the relative amounts of Group IVB metal and Group VIB metal in the catalyst. From these amounts, mole ratios in the form of $XO_2/YO_3$ may be calculated, where X is said Group IVB metal, assumed to be in the form $XO_2$, and Y is said Group VIB metal, assumed to be in the form of $YO_3$. It will be appreciated, however, that these forms of oxides, i.e., $XO_2$ and $YO_3$, may not actually exist, and are referred to herein simply for the purposes of calculating relative quantities of X and Y in the present catalyst. The present catalysts may have calculated mole ratios, expressed in the form of $XO_2/YO_3$, where X is at least one Group IVB metal (i.e., Ti, Zr, and Hf) and Y is at least one Group VIB metal (i.e., Cr, Mo, or W), of up to 1000, e.g., up to 300, e.g., from 2 to 100, e.g., from 4 to 30.

The amount of hydrogenation/dehydrogenation component may be that amount which imparts or increases the catalytic ability of the overall material to catalytically hydrogenate or dehydrogenate a hydrogenatable or dehydrogenatable organic compound under sufficient hydrogenation or dehydrogenation conditions. This amount is referred to herein as a catalytic amount. Quantitatively speaking, the present catalyst may comprise, for example, from about 0.001 to about 5 wt. %, e.g., from about 0.1 to about 2 wt. %, of the hydrogenation/dehydrogenation component, especially when this component is a noble metal.

It may be desirable to incorporate the present catalyst with another material to improve its properties. Such materials include active and inactive materials and synthetic or naturally occurring zeolites as well as inorganic materials such as clays, silica, and/or metal oxides. The latter may be either naturally occurring or in the form of gelatinous precipitates, sols, or gels including mixtures of silica and metal oxides.

The present catalyst includes a hydrogenation-dehydrogenation component to the catalyst. Metals having a strong hydrogenation function are preferred, especially platinum and the other noble metals such as palladium, rhodium, iridium, rhenium, although other metals capable of acting as a hydrogenation component may also be used, for example, nickel, tungsten or other metals of Group VIIIA of the Periodic Table (IUPAC Table), either singly, in mixtures or in combination with other metals. The amount of the noble metal component may be in the range 0.001 to 5 wt.

% of the total catalyst, e.g., from 0.1 to 2 wt. %. Base metal hydrogenation components may be added in somewhat greater amounts. The hydrogenation component can be exchanged onto the support material, impregnated into it or physically admixed with it. If the metal is to be impregnated into or exchanged onto the support, it may be done, for example, by treating the support with a platinum metal-containing ion. Suitable platinum compounds include chloroplatinic acid, platinous chloride and various compounds containing the platinum ammine complex. The metal compounds may be either compounds in which the metal is present in the cation or anion of the compound; both types of compounds can be used. Platinum compounds in which the metal is in the form of a cation of cationic complex, e.g., $Pt(NH_3)_4Cl_2$ are particularly useful, as are anionic complexes such as the vanadate and metatungstate ions. Cationic forms of other metals are also useful since they may be exchanged onto the support or impregnated into it.

The catalyst may be subjected to a final calcination under conventional conditions in order to convert the metal component to the oxide form and to confer the required mechanical strength on the catalyst. Prior to use the catalyst may be subjected to presulfiding.

When a source of hydrogenation metal, such as $H_2PtCl_6$, is used as a source of a hydrogenation-dehydrogenation component in the present catalyst, it may be desirable to subject the present catalyst to extended reducing conditions, e.g., lasting more than 4 hours.

The present catalyst can be shaped into a wide variety of particle sizes. Generally speaking, the particles can be in the form of a powder, a granule, or a molded product, such as an extrudate having particle size sufficient to pass through a 2 mesh (Tyler) screen and be retained on a 400 mesh (Tyler) screen. In cases where the catalyst is molded, such as by extrusion, the catalyst can be extruded before drying or partially dried and then extruded. The present catalyst may be composited with a matrix material to form the finished form of the catalyst and for this purpose conventional matrix materials such as alumina, silica-alumina and silica are suitable with preference given to silica as a non-acidic binder. Other binder materials may be used, for example, titania, zirconia and other metal oxides or clays. The active catalyst may be composited with the matrix in amounts from 80:20 to 20:80 by weight, e.g., from 80:20 to 50:50 active catalyst:matrix. Compositing may be done by conventional means including mulling the materials together followed by extrusion of pelletizing into the desired finished catalyst particles.

The catalyst may be treated by conventional pre-sulfiding treatments, e.g., by heating in the presence of hydrogen sulfide, to convert oxide forms of the metal components to their corresponding sulfides. The catalyst may also be treated with gases, such as $H_2$ and $N_2$, at elevated temperatures prior to contacting with feed to improve catalyst activity.

Hydrocracking Conditions

In the hydrocracking step of the present process, the feedstock is contacted with the aforedescribed catalyst in the presence of hydrogen under hydrocracking conditions of elevated temperature and pressure. Conditions of temperature, pressure, space velocity, hydrogen:feedstock ratio and hydrogen partial pressure which are similar to those used in conventional hydrocracking operations can conveniently be employed herein. Generaaly process temperatures are in the range of from about 500° F. to about 900° F. and preferably from about 600° F. to about 800° F. Total pressure is usually in the range of from about 1000 psig to about 3000 psig with pressures in the range of from about 1500 to about 2500 psig being preferred. The process is operated in the presence of hydrogen with hydrogen partial pressures normally being from about 72 to about 2,305 psig. The hydrogen:feedstock ratio (hydrogen circulation rate) will normally be from about 1,000 to about 8,000 SCF/Bbl and preferably from about 3,000 to about 6,000 SCF/Bbl. The space velocity of the feedstock will normally be from about 0.1 to about 10 LHSV and preferably from about 0.5 to about 2.0 LHSV. The foregoing hydrocracking conditions provide greater than or equal to about 25% feedstock conversion to gasoline (420° F.–) plus distillate (650° F.–) products.

The conversion can be conducted by contacting the feedstock with a fixed stationary bed of catalyst, a fixed fluidized bed or with a transport bed. A simple configuration is a trickle-bed operation in which the feed is allowed to trickle through a stationary fixed bed. With such a configuration, it is desirable to initiate the hydrocracking reaction with fresh catalyst at a moderate temperature which is, of course, raised as the catalyst ages in order to maintain catalytic activity.

The effluent from the hydrocracker is subjected to fractionation after removal of hydrogen and light ends to yield a gasoline product and a higher boiling distillate fraction.

The following example illustrates the hydrocracking process of the present invention.

EXAMPLE 1

The tungsten oxide/zirconia catalyst was prepared by impregnating 15 wt. % tungsten as ammonium metatungstate on dry $Zr(OH)_4$. The hydrous zirconia was prepared by dissolving $ZrOCl_2$ in water, precipitating out with $NH_4OH$, and subsequent overnight refluxing of the precipitate in water set to pH~9 with $NH_4OH$. After tungsten impregnation the catalyst was calcined at 825° C. in air for 4 hours. Hexachloroplatinic acid was impregnated on the tungsten/zirconia catalyst (target 0.5 wt. % Pt) and the resultant mixture calcined at 300° C. in air for 2 hours.

The finished catalyst was pelleted and sized at 24/40 mesh. Ten cc. of catalyst was diluted with sand in a 1;1 ratio and charged to a ½" i.d. microreactor. The catalyst was reduced prior to running by flowing $H_2$ (300 cc/min) at 300° C. for 90 hours. After a standard sulfiding with $H_2S$, the catalyst was contacted with a light cycle oil feed having the following properties as set forth in Table 1.

TABLE 1

| | |
|---|---|
| Carbon, wt % | 87.04 |
| Hydrogen, wt % | 9.97 |
| Nitrogen, wt % | 0.04 |
| Sulfur, wt % | 2.95 |
| Boiling Range, wt % | |
| $C_6$-330° F. | 2.0 |
| 330–420° F. | 7.0 |
| 420–650° F. | 75.5 |
| 650° F.+ | 15.5 |

Two runs were conducted. Table 2 shows the data from each run. The data shows the catalyst of the present invention to be effective in converting cycle oil to 420° F.– liquid products. The data further shows high conversion of heavier cycle oil components (650° F.+) to lighter liquids. The product yield of $C_1$–$C_4$ gases was low. High hydrogen consumption shows substantial hydrogen enrichment of the products. Approximately 90% of the hydrogen enrichment was preserved in the upgraded liquid products.

TABLE 2

| | | |
|---|---|---|
| Temp., ° F. | 725 | 750 |
| LHSV, hr$^{-1}$ | 0.7 | 0.5 |
| H$_2$ Circulation, SCF/Bbl | 4430 | 5360 |
| Pressure, psig | 1900 | 1900 |
| Product Yields, wt % | | |
| H$_2$S | 2.0 | 2.0 |
| C$_1$ + C$_2$ | 0.3 | 0.7 |
| C$_3$ + C$_4$ | 0.3 | 0.6 |
| C$_5$'s | 0.0 | 0.3 |
| C$_6$-330° F. | 5.8 | 8.4 |
| 330–420° F. | 15.0 | 21.6 |
| 420–650° F. | 71.0 | 62.3 |
| 650° F+ | 5.6 | 4.1 |
| Net Conversion to: | | |
| 420° F.- Products | 15.8 | 27.0 |
| 650° F.- Products | 63.9 | 73.5 |
| Wt % Total Products as C$_{6+}$ Liquids | 97.4 | 96.4 |
| Wt % H in Liquid Products | 12.48 | 12.73 |
| H$_2$ Consumption, SCF/Bbl | 1410 | 1590 |
| % Hydrogen Consumption for Enriched Liquid Products | ~ 90 | ~ 88 |

Changes and modifications in the specifically described embodiments can be carried out without departing from the scope of the invention which is intended to be limited only by the scope of the appended claims.

We claim:

1. A process for hydrocracking a hydrocarbon feedstock having an initial boiling point above about 400° F. and an aromatic content greater than about 50 wt. % comprising hydrocracking the hydrocarbon feedstock in the presence of hydrogen at a pressure of at least about 1000 psig in the presence of a catalyst composition comprising a hydrogenation/dehydrogenation catalytic component and an acidic solid catalytic component comprising a Group IVB metal oxide modified with an oxyanion of a Group VIB metal.

2. A process according to claim 1, wherein said hydrogenation/dehydrogenation component comprises a noble metal.

3. A process according to claim 2, wherein said hydrogenation/dehydrogenation component, in addition to said noble metal, further comprises at least one non-noble metal in the form of at least one oxide, hydroxide or metal of at least one element selected from the group consisting of Group VIII metals, Group IVA metals, Group VB metals and Group VIIB metals.

4. A process according to claim 1, wherein said hydrogenation/dehydrogenation component comprises platinum.

5. A process according to claim 2, wherein said hydrogenation/dehydrogenation component further comprises tin.

6. A process according to claim 1, wherein said Group IVB metal oxide comprises zirconia or titania.

7. A process according to claim wherein said Group VIB metal oxyanion is an oxyanion of molybdenum or tungsten.

8. A process according to claim 1, wherein said hydrogenation/dehydrogenation component comprises platinum in the form of an oxide, hydroxide or free metal, said Group IVB metal oxide is zirconium oxide, and said Group VIB metal oxyanion is tungstate.

9. A process according to claim 1, wherein said catalyst comprises a calculated mole ratio of XO$_2$/YO$_3$, where X is said Group IVB metal and Y is said Group VIB metal, of up to 300 and from 0.001 wt. % to about 5 wt. % of said hydrogenation/dehydrogenation component, based upon the total weight of the catalyst.

10. A process according to claim 8, wherein said catalyst comprises a calculated mole ratio of XO$_2$/YO$_3$, where X is said Group IVB metal and Y is said Group VIB metal, of from 2 to 100 and from 0.001 wt. % to about 5 wt. % of said hydrogenation/dehydrogenation component, based upon the total weight of the catalyst.

11. A process according to claim 8, wherein said catalyst comprises a calculated mole ratio of XO$_2$/YO$_3$, where X is said Group IVB metal and Y is said Group VIB metal, of from 4 to 30 and from 0.1 wt. % to about 2 wt. % of platinum, based upon the total weight of the catalyst.

12. The process of claim 1, wherein said hydrocarbon feedstock has an initial boiling point above about of 500° F.

13. The process of claim 1 wherein said hydrocarbon feedstock has an API gravity less than about 25.

14. The process according to claim 1, wherein said hydrocarbon feedstock is hydrotreated prior to hydrocracking.

15. A process according to claim 1, wherein said Group IVB metal oxide is modified with an acidity increasing amount of said oxyanion of a Group VIB metal.

16. A process for hydrocracking a hydrocarbon feedstock having an initial boiling point above about 400° F. and an aromatic content greater than about 50 wt. % comprising hydrocracking the hydrocarbon feedstock in the presence of hydrogen at a pressure of at least about 1000 psig in the presence of a catalyst composition comprising a hydrogenation/dehydrogenation component and an acidic solid component comprising a Group IVB metal oxide modified with an oxyanion of a Group VIB metal, wherein said catalyst is prepared by reacting the oxyanion of the Group VIB metal with a hydroxide or oxide of a Group IVB metal and calcining at a temperature in the range of from about 500° C. to about 900° C.

* * * * *